(12) United States Patent
Tsuboi et al.

(10) Patent No.: US 6,323,224 B1
(45) Date of Patent: *Nov. 27, 2001

(54) AGENTS FOR PRESERVING TECHNICAL MATERIALS AGAINST INSECTS

(75) Inventors: Shinichi Tsuboi, Oyama; Shinzaburo Sone, Yuki; Toru Obinata, Oyama, all of (JP); Otto Exner, Ratingen; Michael Schwamborn, Köln, both of (DE)

(73) Assignee: Nihon Bayer Agrochem K.K., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/543,351

(22) Filed: Oct. 16, 1995

Related U.S. Application Data

(63) Continuation of application No. 07/872,279, filed on Apr. 22, 1993, now abandoned.

(30) Foreign Application Priority Data

Apr. 27, 1991 (JP) .................................................. 3-125172
Dec. 12, 1991 (JP) .................................................. 3-350751

(51) Int. Cl.[7] .................................................. A01N 43/40
(52) U.S. Cl. .......................................................... 514/341
(58) Field of Search .............................................. 514/341

(56) References Cited

U.S. PATENT DOCUMENTS

| 4,276,308 | * | 6/1981 | Ito et al. ............................... | 424/304 |
| 4,678,795 | | 7/1987 | Shiokawa et al. .................... | 514/341 |
| 4,742,060 | | 5/1988 | Shiokawa et al. .................... | 514/252 |

OTHER PUBLICATIONS

85–289794/47, Derwent Publ., (EPO 163,855 = US 4774247 and 4812571).
86–226716/35, Derwent Publ., (EPO 192,060–US 4845106).
87–073950/11, Derwent Publ., (EPO 214,546 = US 4725589 and 4780457).
*Agrochemicals*, vol. 109, 1988, p. 18874.
*Chemical Abstracts*, vol. 114, 1991, p. 201778.

\* cited by examiner

*Primary Examiner*—Allen J. Robinson
(74) *Attorney, Agent, or Firm*—Joseph C. Gil

(57) ABSTRACT

The use of the compounds of the formula (I)

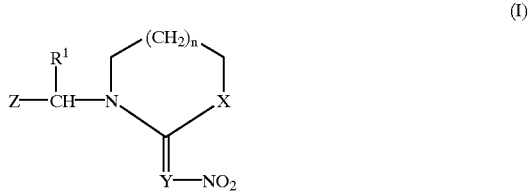

as agents for preserving technical materials against insects.

4 Claims, No Drawings

AGENTS FOR PRESERVING TECHNICAL MATERIALS AGAINST INSECTS

This application is a continuation of application Ser. No. 07/872,279, filed on Apr. 22, 1992 now abandoned.

The present invention relates to the use of known nitromethylene or nitroimino compounds as agents for combating technical materials destroying insects in order to preserve these materials.

The present invention also relates to compositions useful for combating these insects, preserving technical materials completely, i.e. not only against insects but also against fungi, bacteriae and algae and for treating soil to protect technical materials against termite infestations.

The invention furthermore relates to processes for treating technical materials and for soil treatment against termite infestations.

The compounds and their insecticidal use in the field of plant protection has already been known. Compare for example with EP-A 163855 and EP-A 192060.

Insecticidal agents and compositions of said compounds and their use to preserve technical materials completely and to treat soil against-termite infestations have not been known up to now.

Different insects are known as pests infesting technical materials so that due to serious damages caused thereby undesirable effects on living environment and cultural assets principally made of these materials have posed a social problem, urgently requiring effective controlling of the pests. Termites are known as important examples of these pests.

At present, use for combating technical materials destroying insects has been made of organophosphorus insecticides such as phoxim [0-(α-cyanobenzylideneamino) 0,0-diethylphosphorothioate], chloropyriphos [0,0-diethyl-3,5,6-trichloro-2-pyridylphosphorothioate], etc., as well as pyrethroides series insecticides such as permethrin [5-benzyl-3-furylmethyl-3-(2-methoxy-carbonyl-1-propenyl)-2,2-dimethylcyclopropane carboxylate], decamethrin [α-cyano-3-phenoxybenzyl d,l-cis-3-(2,2-dibromovinyl)-2,2-dimethyl cyclopropane carboxylate], cypermethrin [α-cyano-3-phenoxybenzyl (±) cis, trans-3-(2, 2-dichlorovinyl)-2,2-dimethylcyclopropanecarboxylate], fenvalerate [(RS)-α-cyano-3-phenoxybenzyl (RS)-2-(4-chlorophenyl)-3-methylbutyrate], cyflutrine [cyano-(4-fluoro-3-phenoxyphenyl) methyl-3-(2,2-dichloroethenyl)-2, 2-dimethyl-cyclopropane carboxylate].

However, the above-mentioned insecticides are unsatisfactory as far as effective concentration and the long lasting effect are concerned.

It has been found that the known compounds of the formula (I)

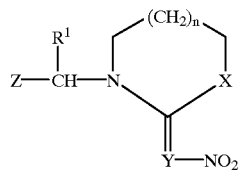

(I)

wherein X is NH or S,
Y is CH or N
Z is 2-chloro-5-pyridyl or 2-chloro-5-thiazolyl, $R^1$ is hydrogen or methyl, and
n is 0 or 1,
exhibit powerful insecticidal properties on material destroying insects and preferably on termites.

The compounds according to the invention of the formula (I) surprisingly exhibit an extremely strong insecticidal action on material destroying insects and the function is substantially superior to that of known insecticidal agents.

The compounds of the formula (I) can be used to preserve technical materials against insects.

In the formula (I), the individual residues have the following preferable meanings:
X is NH or S,
Y is CH or N,
Z is 2-chloro-5-pyridyl,
$R^1$ is hydrogen, and
n is 0 or 1.

As examples of the active substances to be used according to the invention, the following ones are particularly preferred:

1-(6-chloro-3-pyridylmethyl)-2-nitromethylene-imidazolidine, 3-(6-chloro-3-pyridylmethyl)-2-nitromethylene-thiazolidine, 1-(6-chloro-3-pyridylmethyl)-2-nitroimino-imidazolidine, 1-(6-chloro-3-pyridylmethyl)-2-nitromethylene-tetrahydropyrimidine, and 3-(6-chloro-3-pyridylmethyl)-2-nitromethylene-tetrahydro-2H-1,3-thiazine.

The active substances to be used according to the invention exhibit powerful insecticidal effects against material destroying insects.

They can therefore be used in insecticidal agents for combating material destroying insects and preserving technical materials. They can also be used for soil treatment against termite infestation.

As individual examples of technical materials preserved by means of the insecticidal agents according to the present invention the following ones can be mentioned: wood or composite wood-materials (such as pressed wood, particle board, chip board, wafer board, plywood, wood laminated material, freshly cut timber/lumber etc.), paper,leather or leather products, natural or synthetic polymers, textiles.

Preferable materials are wood or composite wood-materials.

As individual examples of insects to be combated or controled by the active substances of formula (I) according to the present invention the following ones can be mentioned:

Order Isoptera
  Mastotermitidae
  Kalotermitidae such as Kalotermes spp.
    Cryptotermes spp. etc.
  Termopsidae such as Zootermopsis spp. etc.
  Rhinotermitidae such as Reticulitermes spp.
    Heterotermes spp.
    Coptotermes spp. etc.
  Termitidae such as Amitermes spp.
    Nasutitermes spp.
    Acanthotermes spp.
    Mikrotermes spp. etc.
Order Coleoptera
  Lyctidae such as *Lyctus brunneus* etc.

Bostrychidae such as *Bostrychus capucinus*
*Dinoderus minutus* etc.
Anobiidae such as *Anobium punctatum*
*Xyletinus peltatus*
*Xestobium rufovillosum*
*Ptilinus pectinicomis* etc.
Cerambycidae such as *Hylotrupes bajulus*
*Hesperophanus cinereus*
*Stromatium fulvum*
*Chlorophorus pilosus* etc.
Oedemeridae
Serropulpidae
Curculionidae
Seolytida
Platypodidae
Order Hymenoptera
Siricidae such as Sirex spp.
Urocerus spp.
Formicidae such as Camponotus spp.

In the above Isopterous insects, especially, there may be mentioned as examples of termites in Japan:

*Deucotermes speratus,*

*Coptotermes formosanus,*

*Glyptotermes fucus,*

*Glyptotermes satsumensis,*

*Glyptotermes nakajimai,*

*Glyptotermes Kodamai,*

*Incisitermes minor,*

*Neotermes koshunensis,*

*Cryptotermes domesticus,*

*Hodotermopsis japonica,*

*Reticulitermes miyatakei,*

*Odontotermes formosanus,*

*Nasutitermes takasagoensis,*

*Capritermes nitobei* and so on.

The active compounds of the general formula (I) in the present invention can be prepared into the customary formulations, such as solutions, emulsions, suspensions, powders, foams, pastes, granules, aerosols, natural and synthetic materials impregnated with active compounds, and micro-capsules.

These formulations may be produced in a known manner, for example, by mixing the active compounds with extenders, that is to say liquid or liquefied gaseous or solid diluents or carriers, optionally with the use of surface-active agents, that is to say emulsifying agents, dispersing agents, and/or foam-forming agents. In the case of using water as an extender, organic solvents can, for example, also be used as auxiliary solvents.

As liquid diluents or carriers can be mentioned, for example, aromatic hydrocarbons, such as xylene, toluene and alkyl naphthalenes, chlorinated aromatic or chlorinated aliphatic hydrocarbons, such as chlorobenzenes, chloroethylenes and methylene chloride, aliphatic or alicyclic hydrocarbons, such as cyclohexane or paraffins, for example, mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulfoxide, as well as water.

By liquefied gaseous diluents or carriers are meant liquids which are gaseous at normal temperature and under normal pressure, for example, aerosol propellants, such as halogenated hydrocarbons as well as butane, propane, nitrogen and carbon dioxide.

As solid diluents there may be used ground natural minerals, such as kaolins, clays, talc, chalk, quartz, attapulgite, montmorillonite or diatomaceus earth, and ground synthetic minerals, such as highly-dispersed silicic acid, alumina and silicates.

As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used nonionic and ionic emulsifiers, such as polyoxyethylene-fatty acid esters, polyoxyethylene-fatty alcohol ethers, for example, alkylaryl polyglycol ethers, alkylsulfonates, alkylsulfates, arylsulfonates as well as albumin hydrolysis products. Dispersing agents include, for example, lignin sulfite waste liquors and methyl cellulose.

Adhesives such as carboxymethyl cellulose and natural and synthetic polymers, (such as gum arabic, polyvinyl alcohol and polyvinyl acetate) can be used in the formulations in the form of powders, granules or emulsifiable concentrations.

It is possible to use colorants such as inorganic pigments, for example, iron oxide, titanium oxide and Prussian Blue, and organic dyestuffs, such as alizarin dyestuffs, azo dyestuffs or metal phthalo-cyanine dyestuffs, and trace elements, such as salts of iron, manganese, boron, copper, cobalt, molybdenum and zinc.

The formulations, in general, contain from 0.001 to 95 percent by weight of active compound, preferably from 0.5 to 90 percent by weight.

Furthermore, the active compound of the present invention having the formula (I) can be present as a mixture with a synergist in a formulation or a use form, of the type that is commercially useful. The term "synergist" denotes a compound which is not active in itself, but promotes the action of an active compound. The content of the active compounds having the general formula (I) of the present invention in conmercially useful formulations can vary within a wide range. The active compound concentration.of the formulation for use is, for example, from 0.0000001 to 100 percent by weight, preferably from 0.0001 to 1 percent by weight.

In order to protect the above-mentioned materials completely, i.e. not only against material destroying insects but also against fungi, bacteria and algae, they can be treated with compositions containing at least one insecticidally active compound of the formula (I) and at least one biological active fungicide, bactericide or algizide.

Wood or composite wood-materials can preferably be treated with a composition containing a) an insecticidally effective amount of a compound of the formula (I) or mixtures thereof and b) a fungicidally effective amount of at least one compound selected from the group of
Trihalosulfenyl-Compounds such as
N-Dichlorofluoromethylthio-N',N'-dimethyl-N-phenyl-sulfuric acid diamide (Dichlofluanide)
N-Dichlorofluoromethylthio-N',N'-dimethyl-N-p-toluylsulphamide (Tolylfluanide)
N-Trichloromethylthiophthalimide (Folpet)
N-Dichlorofluoromethylthiophthalimide (Fluorfolpet) etc.

Iodine-Compounds such as
  3-Iodo-2-propynyl-butylcarbamate (IPBC)
  3-Iodo-2-propynyl-hexylcarbamate
  3-Iodo-2-propynyl-cyclohexylcarbamate
  3-Iodo-2-propynyl-phenylcarbamate
  Diiodmethyl-p-tolylsulphone (Amical 48) etc.
Phenols such as
  ortho-Phenylphenol
  Tribromophenol
  Tetrachlorophenol
  Pentachlorophenol etc.
Azole-Compounds such as
  1-(4-Chlorophenoxy)-3,3-dimethyl-1-(1H-1,2,4 triazol-1-yl)-2-butanone (Triadimefon)
  β-(4-Chlorophenoxy)-α-(1,1 dimethyl-ethyl)-1H-1, 2,4 triazole-1-ethanol (Triadimenol)
  ±α[2-(4-chlorophenyl) ethyl]-α-(1,1-dimethylethyl)-1H-1,2,4-triazole-1-ethanol (Tebuconazole)
  1-[2(2,4-dichlorophenyl) 4-propyl-1,3-dioxolan-2-ylmethyl]-1H-1,2,4-triazole (Propiconazol)
  1-[2(2,4-dichlorophenyl)-1,3-dioxolan-2-ylmethyl]-1H-1,2,4-triazole (Azaconazol)
  (RS)-2(2,4-dichlorophenyl)-1-(1H-1,2,4 triazol-2-yl)-2-ol (Hexaconazol)
  1-N-propyl-N-[2-(2,4,6-trichlorophenoxy) ethyl] carbamoylimidazol (Prochloraz) etc.
Tin Compounds such as
  Tributyl tin octoate
  Tributyl tin oleate
  Bistributyl tin oxide
  Tributyl tin naphthenate
  Tributyl tin phosphate
  Tributyl tin benzoate etc.
Thiocyanate Compounds such as
  Methylenebisthiocyanate (MBT)
  2-Thiocyanomethylthiobenzothiazole (TCMTB) etc.
Quarternary Ammonium Compounds such as
  Benzyl-dimethyl-tetradecylammoniumchloride
  Benzyl-dimethyl-dodecylammoniumchloride etc.
Benzimidazole Compounds such as
  2-(2'-Furyl)-1H-benzimidazole (Fuberidazole)
  Methylbenzimidazol-2-ylcarbamate (BCM)
  2-(4$^1$-thiazolyl) benzimidazole (Thiabendazole)
  Methyl (1-butylcarbamoyl)-2-benzimidazole carbamate (Benomyl)
Isothiazolinone Compounds such as
  N-Methylisothiazolin-3-one
  5-Chloro-N-methylisothiazolin-3-one
  4,5-Dichloro-N-octylisothiazolin-3-one
  N-Octylisothiazolin-3-one
Morpholine Compounds such as
  $C_{14}$–$C_{11}$-4-Alkyl-2,6-dimethylmorpholine (Tridemorph)
Pyridine Compounds such as
  1-Hydroxy-2-pyridine-thione and Sodium Iron, Manganese or Zinc-Salt thereof
  Tetrachloro-4-methyl sulphonyl pyridine
N-Cyclohexyldiaziniumdioxy Compounds such as
  Tris-(N-cyclohexyldiaziniumdioxy) aluminium
  Bis-(N-cyclohexyldiaziniumdioxy) copper
Naphthenate Compounds such as
  Zincnaphthenate
Quinoline Compounds such as the cooper salt of
  8-hydroxy-quinoline
Nitriles such as
  1,2,3,5-Tetrachloro-4,6-cyanobenzene
Boric compounds such as boric acid, borax, borates
Ureas such as N'(3,4-dichlorophenyl)-N,N-dimethylurea
Furane derivatives such as Furmecyclox These fungicidally effective compounds are added to the composition in order to prevent wood or wood materials not only against wood destroying insects but also against
  Wood-discoloring fungi such as
    Ascomycetes (*Caratocystis minor*)
    Deuteromycetes (*Aspergillus niger, Aureobasidium pullulans, Dactyleum fusarioides, Penicillium Variabile, Sclerophoma pithyophila, Scopularia phycomyces, Trichoderma viride, Trichoderma liguorum*)
    Zygomycetes (*Mucor spinosus*)
  and/or
  Wood-destroying fungi such as
    Ascomycets (*Chetomium alba-arenulum, Chaetonium globosum,*
    *Humicola grisea, Petriella setifera, Trichurus spiralis*)
    Basidiomycetes (*Coniophera puteana*
      *Coriolus versicolor*
      *Donbiopora expansa*
      *Glenospora graphii*
      *Gloeophyllum abietinum*
      *Gloeophyllum adoratum*
      *Gloeophyllum protactum*
      *Gloeophyllum trabeum*
      *Gloeophyllum sepiarium*
      *Lentinus cyathioformes*
      *Lentinus edodes*
      *Lentinus lepideus*
      *Lentinus squavrolosus*
      *Paxillus panuoides*
      *Pleurofus ostreatus*
      *Poria placenta*
      *Poria monticola*
      *Poria vaillantii*
      *Poria vaporia*
      *Serpula himantoides*
      *erpula lacrymans*
      *Tyromyces palustris*)
    Deuteromycetes (*Cladosporium herbarum*).

Generally the compositions also will include at least one additional diluent, emulsifier, melting agent, organic binding agent, auxiliary solvents, processing additives, fixatives, plasticizers, UV-stabilizers or stability enhancers, dyes (water soluble, water insoluble), color pigments, siccatives, corrosion inhibitors, antisettlement agents, additional insecticides (such as insecticidal carbamates, organophosphorus compounds, halogenated hydrocarbons, pyrethroides etc.), anti skinning agents and the like.

The above-mentioned additional ingredients and their use are described in prior art. (EP-A 0370665, DE-A 3531257, DE-A 3414244).

The compositions according to the present invention generally comprise from about $10^{-6}$ to 30 parts by weight, preferably from about 0.0005 to 15 parts by weight and more preferably from 0.005 to 2 parts by weight of the insecticide of formula (I) and from 0.01 to 90 parts by weight, preferably from about 0.05 to 50 parts by weight and more preferably from 0.1 to 30 parts by weight of at least one of the above-mentioned fungicides.

The compositions can be provided as ready for use products or as concentrates, which have to be diluted prior to use.

The compositions can be applied by means of brushing, spraying, dipping, double vacuum and the like as known in the art. The compositions can be prepared by any technique known in the art.

The content of the present invention will be concretely explained by way of the following examples but the present invention should not be limited only thereto.

EXAMPLES FOR COMPOSITIONS
*Remark: The Percentages are Given in Percent by Weight Example 1

0.005% 1-(6-chloro-3-pyridylmethyl)-2-nitroimino-imidazolidine (imidacloprid)
5% Butylglycol
94.995% Mineral spirits Example 2

Impregnating Agent/Primer 0.01% Imidacloprid
0.5% Dichlofluanide
1.% Tebuconazole
9.7% Alkyd resin (solid)
88.79% Mineral spirits Example 3

Wood Stain/Low Build 0.01% imidacloprid
0.5% Dichlofluanide
1.2% Tebuconazole
21% Alkyd resin (solid)
2% Pigment
4% Antisettlement additive, dryes etc.
71.29% Mineral spirits Example 4 Wood Stain/High Build 0.015% imidacloprid
0.6% Dichlofluanide
1.5% Tebuconazole
40% Alkyd resin
2% Pigment
4% Antisettlement additive, dryer etc.
48.115% Mineral spirits Example 5

Soil Treatment

20% imidacloprid
8% ethylene glycol
3% emulsifiers
0.25% thickeners
68.75% distilled water Example 6

Wood Brushing 0.1% imidacloprid
1% 3-bromo-2,3-diiodo-2-propenyl ethylcarbonate
98.9% organic solvents Example 7

Wood Brushing 0.1% imidacloprid
1.5% 4-chlorophenyl-3-iodopropargylformal
98.4% organic solvents Example 8

Formicidal Test

Compounds Under Test
 Examples of the active compounds according to the present invention
  I.1: 1-(6-chloro-3-pyridylmethyl)-2-nitromethylene-imidazolidine
  I.2: 3-(6-chloro-3-pyridylmethyl)-2-nitromethylenethiazolidine
  I.3: imidacloprid
Comparative Compounds
 A: phoxim
 B: chlorpyriphos
Preparation of Test Formulation:
 Solvent: 3 parts by weight of xylene
 Emulsifier: 1 part by weight of polyoxyethylene-alkylphenyl-ether
 To prepare a suitable formulation of the active compound, 1 part by weight of each of the active compounds was mixed with the above-mentioned amount of the solvent containing the above-mentioned amount of the emulsifier, and the mixture was diluted with water to a predetermined concentration.
Test Method:
 1 ml of the aqueous solution prepared in the above-mentioned procedure was uniformly applied using a pipette onto a filter paper that was placed in petri dish of 9 cm diameter. Ten head of worker termites (*Coptotermes formosanus*) were replaced into the petri dish and it was kept in a constant temperature chamber at 25° C.

After four days, the mortality of the termites was investigated. This test procedure was carried out in duplicate per each concentration of the active compounds under test.

The test results are shown in Table 1.

TABLE 1

| Compound | Concentration of active compound (ppm) | Mortality of termites after four days (%) |
| --- | --- | --- |
| I.1 | 40 | 100 |
|  | 8 | 100 |
|  | 1.6 | 100 |
|  | 0.32 | 100 |
| I.2 | 40 | 100 |
|  | 8 | 100 |
|  | 1.6 | 100 |
|  | 0.32 | 100 |
| I.3 | 40 | 100 |
|  | 8 | 100 |
|  | 1.6 | 100 |
|  | 0.32 | 100 |
| A | 40 | 100 |
|  | 8 | 100 |
|  | 1.6 | 100 |
|  | 0.32 | 90 |
| B | 40 | 100 |
|  | 8 | 100 |
|  | 1.6 | 100 |
|  | 0.32 | 100 |
| Untreated |  | 0 |

Example 9

Test on Residual Effect

Small blocks of Japanese redpine tree (2 cm×2 cm×2 cm) were soaked for one minute into the aqueous solution prepared by the similar procedure to Example 8.

After air-dried, they were kept in a constant temperature chamber at 40° C. for four weeks. Then each of the thus treated blocks was placed in a polymeric cup (10 cm diameter) containing 150 ml of sandy loam of 20% moisture content. Into each of the polymeric cups, 100 head of working termites and 10 head of soldier termites (*Coptotermes formosanus*) were released. After three weeks, the degree of xylophagous damage in the block and the mortality of the termites were investigated.

Three tests were carried out in duplicate 25° C., and the results are shown in Table 2.

The index of xylophagous damage observed on the test blocks:

0: No damage
0.5: One to two traces of damage each having a depth of about 1 mm from the block surface
1: One to two evident damages each having a depth from 1 to 2 mm from the block surface
2: More than three evident damages or more than one deep trace of damage having a depth of more than 2 mm from the block surface
3: More than three deep damages
4: Evidently damaged zone covering up to about one third of the whole surface area of the block
5: Evidently damaged zone covering more than one third of the whole surface area of the block

TABLE 2

| Compound | Concentration of active compound (ppm) | Mortality termites after three weeks (%) | Degree of xylophagous damage in the pine tree block (0–5) |
|---|---|---|---|
| I.1 | 40 | 100 | 0 |
|  | 8 | 100 | 0 |
|  | 1.6 | 100 | 0 |
|  | 0.32 | 98 | 0.5 |
| I.2 | 40 | 100 | 0 |
|  | 8 | 100 | 0 |
|  | 1.6 | 100 | 0 |
|  | 0.32 | 100 | 0 |
| I.3 | 40 | 100 | 0 |
|  | 8 | 100 | 0 |
|  | 1.6 | 100 | 0 |
|  | 0.32 | 100 | 0 |
| A | 40 | 25 | 3 |
|  | 8 | 0 | 5 |
|  | 1.6 | 0 | 5 |
|  | 0.32 | 0 | 5 |
| B | 40 | 100 | 0 |
|  | 8 | 78 | 1 |
|  | 1.6 | 0 | 3 |
|  | 0.32 | 0 | 5 |
| Untreated |  | 0 | 5 |

Example 10

Toxic Value Against Larvae of *Hylotrupes bajulus*

The toxicity against larvae of *Hylotorupes bajulus*, using wood samples treated with the active compound I.3 provided in Example 8 in chloroform having concentrations of $1.44 \times 10^{-5}\%$, $1.44 \times 10^{-4}\%$, $7.2 \times 10^{-3}\%$, and $1.44 \times 10^{-2}\%$ was determined according to the detailed description of DIN EN 47 (edition 1990, Beuth Verlag GMBH) which is concerned with the European standard method prescribed by the European Committee for standardization concerning wood preservatives, determination of the toxic value against larvae of *Hylotrupes bajulus*.

An outline of the method is as follows: (see DIN EN 47 for detail)

Five wood-samples (50 mm×25 mm×15 mm) which are treated by the active compound beforehand (impregnation treatment in vacuum) are provided and in each specimen, a regular pattern of six holes are bored, and then one head of the larvae is inserted per a hole.

After four weeks, the specimens are cut up in turn and the number of live/dead of larvae is determined.

In determination, where a live larvae is identified in a specimen, then the remaining specimens without cutting up are stored for a further eight weeks, and afterward, the number of live/dead larvae is determined.

From this test, the Toxic threshold value was between $1.08 \text{ g/m}^3$ and $10.8 \text{ g/m}^3$ of the active compound I.3.

The results are shown in Table 3.

TABLE 3

| Duration of the test in weeks | Concentration of the impregnating solution (%) | Quantity of active compound concentrate absorbed in g/m³ wood | | | State of the larvae at the end of the test deed | | |
|---|---|---|---|---|---|---|---|
| | | min. | max. | M-value | deed no wood digested | wood digested | living | not found |

| Duration (weeks) | Conc. (%) | min. | max. | M-value | no wood digested | wood digested | living | not found |
|---|---|---|---|---|---|---|---|---|
| 4 | 0.0144 | 82.08 | 116.64 | 103.97 | 27 | 3 | 0 | 0 |
|  | 0.0072 | 45.36 | 56.88 | 52.85 | 29 | 1 | 0 | 0 |
|  | 0.00144 | 10.08 | 11.23 | 10.80 | 4 | 6 | 1 (*1) | 1 |
| 12 | 0.00144 (*2) | 9.94 | 11.66 | 10.80 | 6 | 11 | 0 | 1 |
|  | 0.000144 | 0.95 | 1.21 | 1.08 | 4 | 12 | 11 | 3 |
|  | 0.0000144 | 0.09 | 0.12 | 0.11 | 1 | 4 | 23 | 2 |
| 12 | control samples | impregnated with chloroform not treated | | | 2 | 2 | 24 | 2 |

Note:

(*1) One live larvae was found in the second specimen.

(*2) The remaining three specimens were tested for further eight weeks (12 weeks in total).

Comparative values of W. Metzner et al in "Holz als Rohund Werkstoff, 35 (1977) 233–237", table 6 on page 236.

TABLE 4

| Insecticide | toxic value (g/m³) | Insecticide | toxic value (g/m³) |
|---|---|---|---|
| DDT | 5–10 | Bassa (Baycarb) | 17–30–44 |
| Diazinon | 12–18–32 | Propoxur | 18–30 |
| Phoxim | 7–12 | Carbaryl | 12–18 |
| Chlorophoxim | 12–20–32 | | |

Example 11

Effectiveness Against the Termite Species *Reticulitermes santonensis*

The toxicity against *Reticulitermes santonensis* of solutions containing the active compound I.3 in chloroform having the concentrations mentioned in Example 10 was determined according to the detailed description of DIN EN 117 Edition 1981 which is concerned with the European standard method prescribed by the European Committee for standardization concerning wood preservatives, determination of the toxic value against Reticulitermes santonesis.

An outline of the method is as follows: (see DIN EN 117 for detail)

The same three wood-samples with impregnation treatment in vacuum as in Example 10 are provided.

They are exposed to 250 workers, 1 soldier and 1 nymph per batch for eight weeks, and afterward, the number of live/dead larvae is determined.

From this test, the toxic threshold value was between 0.135 g/m³ and 1.344 g/m³ of the active compound I.3.

The evaluation was made by the following standard:

*Rating Values:

0=no attack

1=attempted attack

2=slight attack

3=average attack

4=strong attack

The results are shown in Table 5.

TABLE 5

| Concentration of protect agent tested in % (m/m) | No. of wood sample | Quantity of solution absorbed per wood sample in g/m³ | Quantity of protective agent absorbed per wood sample in g/m³ | average quantity absorbed in g/m³ | surviving workers % | Soldiers (S) or nymphs (N) | * rating |
|---|---|---|---|---|---|---|---|
| 1.44 × 10⁻⁵% | 1 | 17.75 | 0.136 | 0.135 | 55 | S/N | 4 |
| | 2 | 17.47 | 0.134 | | 51 | S/N | 4 |
| | 3 | 17.69 | 0.136 | | 58 | S/N | 4 |
| 1.44 × 10⁻⁴% | 4 | 17.75 | 1.363 | 1.344 | 0 | — | 1 |
| | 5 | 17.39 | 1.336 | | 0 | — | 1 |
| | 6 | 17.37 | 1.334 | | 0 | — | 1 |
| 1.44 × 10⁻³% | 7 | 17.54 | 13.471 | 13.463 | 0 | — | 1 |
| | 8 | 17.56 | 13.486 | | 0 | — | 1 |
| | 9 | 17.49 | 13.432 | | 0 | — | 1 |
| 7.20 × 10⁻³% | 10 | 17.29 | 66.3936 | 68.211 | 0 | — | 0 |
| | 11 | 18.03 | 69.2352 | | 0 | — | 0 |
| | 12 | 17.97 | 69.0048 | | 0 | — | 0 |
| 1.44 × 10⁻²% | 13 | 17.79 | 136.627 | 136.627 | 0 | — | 0 |
| | 14 | 17.72 | 136.090 | | 0 | — | 0 |
| | 15 | 17.86 | 137.165 | | 0 | — | 0 |
| control samples diluent (chloroform) | 16 | 17.72 | 0 | 0 | 50 | —/N | 4 |
| | 17 | 18.15 | 0 | | 57 | S/N | 4 |
| | 18 | 17.77 | 0 | | 48 | S/N | 4 |
| control samples untreated | 19 | 0 | 0 | 0 | 55 | S/N | 4 |
| | 20 | 0 | 0 | | 62 | S/N | 4 |
| | 21 | 0 | 0 | | 64 | —/N | 4 |

Comparative values of W. Metzner et al in "Holz als Rohund Werkstoff,"35 (1977) 233–237, table 10 on page 236.

TABLE 6

| Insecticide | toxic value g/m³ | Insecticide | toxic value g/m³ |
|---|---|---|---|
| DDT | >1500 | Chlorophoxim | 500 |
| Dieldrin | 50 | Bassa | 500 |
| Lindan | 75 | Propoxur | 140 |

TABLE 6-continued

| Insecticide | toxic value g/m$^3$ | Insecticide | toxic value g/m$^3$ |
|---|---|---|---|
| Ethylparathion | 200 | Carbaryl | 1100 |
| Phoxim | 400 | | |

What is claimed is:

1. A method of protecting a wood product selected from the group consisting of wood and wood composites against attack by insects comprising applying directly thereto an amount sufficient to effect protection thereof of the compound 1-(6-chloro-3-pyridylmethyl)-2-nitroimino-imidazolidine, wherein said compound is applied in manner selected from the group consisting of i) soaking said wood product in or with said compound, ii) impregnating said wood product with said compound, iii) brushing said compound onto said wood product, iv) spraying said compound onto said wood product, and v) dipping said wood product in said compound and wherein after three weeks said imidazolidine compound shows improved long lasting effects.

2. A method according to claim 1, wherein the 1-(6-chloro-3-pyridylmethyl)-2-nitroimino-imidazolidine is in the form of a composition comprising from $10^{-6}$ to 30 parts by weight of 1-(6-chloro-3-pyridylmethyl)-2-nitroimino-imidazolidine.

3. A method according to claim 1, wherein the 1-(6-chloro-3-pyridylmethyl)-2-nitroimino-imidazolidine is in the form of a composition comprising from 0.32 to 40 ppm 1-(6-chloro-3-pyridylmethyl)-2-nitroimino-imidazolidine.

4. A method according to claim 1, wherein the wood product is a wood composite selected from the group consisting of pressed wood, particle board, chip board, plywood and wood laminated materials.

* * * * *

(12) EX PARTE REEXAMINATION CERTIFICATE (8648th)
United States Patent
Tsuboi et al.

(10) Number: US 6,323,224 C1
(45) Certificate Issued: Nov. 1, 2011

(54) AGENTS FOR PRESERVING TECHNICAL MATERIALS AGAINST INSECTS

(75) Inventors: Shinichi Tsuboi, Oyama (JP); Shinzaburo Sone, Yuki (JP); Toru Obinata, Oyama (JP); Otto Exner, Ratingen (DE); Michael Schwamborn, Köln (DE)

(73) Assignee: Bayer Cropscience AG, Monheim am Rhein (DE)

Reexamination Request:
No. 90/010,399, Jan. 30, 2009

Reexamination Certificate for:
Patent No.: 6,323,224
Issued: Nov. 27, 2001
Appl. No.: 08/543,351
Filed: Oct. 16, 1995

Related U.S. Application Data

(63) Continuation of application No. 07/872,279, filed on Apr. 22, 1992, now abandoned.

(51) Int. Cl.
*A01N 43/50* (2006.01)
*A01N 43/54* (2006.01)
*A01N 43/78* (2006.01)
*A01N 43/86* (2006.01)
*A01N 43/48* (2006.01)
*A01N 43/72* (2006.01)
*A01N 51/00* (2006.01)
*B27K 3/34* (2006.01)

(52) U.S. Cl. ........................................ 514/341
(58) Field of Classification Search .................. 514/341
See application file for complete search history.

(56) References Cited

To view the complete listing of prior art documents cited during the proceeding for Reexamination Control Number 90/010,399, please refer to the USPTO's public Patent Application Information Retrieval (PAIR) system under the Display References tab.

*Primary Examiner* — Dwayne C Jones

(57) ABSTRACT

The use of the compounds of the formula (I)

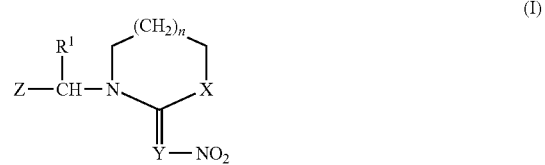

as agents for preserving technical materials against insects.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-4 is confirmed.

* * * * *